United States Patent
Aydelotte et al.

(10) Patent No.: US 6,290,678 B1
(45) Date of Patent: Sep. 18, 2001

(54) HIGH CONTRAST SYRINGE

(76) Inventors: A. Susan Aydelotte; Fred A. Aydelotte, both of 2599 Lake Jackson Cir., Apopka, FL (US) 32703

(*) Notice: Subject to any disclaimer, the term of this patent is extended or adjusted under 35 U.S.C. 154(b) by 0 days.

(21) Appl. No.: 09/585,092

(22) Filed: Jun. 1, 2000

Related U.S. Application Data

(60) Provisional application No. 60/136,824, filed on Jun. 1, 1999.

(51) Int. Cl.⁷ .................................... A61M 5/00
(52) U.S. Cl. ................................................. 604/187
(58) Field of Search .................... 604/187, 189, 604/207, 218

(56) References Cited

U.S. PATENT DOCUMENTS

| 827,383 | * | 7/1906 | McElroy et al. | ............ 604/207 |
| 2,432,605 | * | 12/1947 | Barach | ............ 604/207 |
| 5,242,405 | * | 9/1993 | Howe | ............ 604/189 X |

* cited by examiner

Primary Examiner—Manuel Mendez
(74) Attorney, Agent, or Firm—Kimberly A. Chasteen

(57) ABSTRACT

A syringe having color demarcation features to enhance readability. Said syringe having a central body portion that is a barrel having a proximal and distal end along a central longitudinal axis that acts a reservoir for fluid inside the syringe. The side wall of the barrel is relatively transparent having volume demarcations in contrasting colors to increase the readability of the demarcations. A plunger and coupled seal member can be engaged with the proximal end of the barrel creating a liquid tight reservoir inside the syringe. The seal member can be made a contrasting color to further enhance the readability of the demarcations.

19 Claims, 1 Drawing Sheet

HIGH CONTRAST SYRINGE

This Application claims benefit of provisional application Ser. No. 60/136,824 filed Jun. 1, 1999.

BACKGROUND OF THE INVENTION

1. Technical Field of the Invention

The present invention relates generally to medical instruments and more particularly to a syringe, which uses color demarcations on a syringe barrel to increase readability of the volume of fluid in the barrel.

2. Discussion of the Related Art

A typical syringe is comprised of several distinct components including a barrel, plunger and cannula or needle.

The barrel, usually made from plastic, having a proximal and distal end, acts as a reservoir for fluid, usually medicine. The proximal end is open to receive a plunger and coupled seal member or cap. The distal end is connected to a cannula or adaptable to a hypodermic needle assembly to permit fluid to be drawn or expelled through the distal end.

The seal member is attached to the plunger and provides a means of creating a liquid tight seal between the seal member and the syringe barrel so that movement of the plunger along the barrel causes liquid to be drawn into or expelled out of the syringe through the distal end. The seal member is moved through the syringe barrel by applying axial force to the plunger.

The plunger is attached to a disc member on the end opposed to the seal member. The disc member creates a surface to apply force to the plunger. The overall length of the plunger exceeds the length of the barrel thereby permitting its operation by engaging the disc member even when the seal member reaches the distal end of the barrel.

Syringes usually contain demarcations such as volume measuring indicia on the side of the barrel to indicate the volume of liquid contained within the syringe. The demarcations are usually black and are easily skewed during operation by a black seal tipped plunger.

Enhancements to standard volume measuring demarcations are desirable to provide a syringe for administrating medication that can be used in a far easier manner than the standard black on black syringe. Many patients that suffer from diabetes or other diseases causing decreased visual acuity could benefit from easy to read volume markers and numbers on a syringe. Diabetics and their caretakers, such as the inventors, frequently experience blurry vision and loss of the ability to distinguish serial lines commonly found on the black on black model of a standard syringe.

Most hypodermic syringe barrels are made of transparent plastic with black volume measuring demarcations along their side walls. The use of alternating color instead of black for the volume measuring increases the user's ability to distinguish between the demarcations. A colored seal member rather the black seal shown in the art would also increase the user's ability to properly read the volume level.

Previous syringes have used a color contrast means integral to the syringe for the purpose of amplifying the volume measuring indicia. Such a device is taught in the U.S. Pat. No. 5,242,405 to Howe. Howe teaches an opaque color contrast means on the syringe barrel to improve readability of the volume measuring indicia. However, the addition of graphics and opaque members may ultimately skew the view of the volume demarcations whereas coloring the demarcations themselves would not create this hindrance, but would enhance the user's ability to properly gauge the dosage in the barrel. Additionally, the introduction of a colored seal member on the plunger would further aid in accurate measurements of the liquid in the barrel.

Even though the art teaches means for improving the readability of volume measuring indicia on syringes through contrasting means such as opaque coatings, there is still a void in this field that could be filled by the present invention which provides a color enhanced syringe that is easy to read, use and manufacture using existing technology with the addition of strategically placed color demarcations on the barrel of a standard syringe without the use of additional markings on or treatments to the syringe that may obscure the visual field. Using color on the seal member of the plunger as demonstrate by the present invention, improves readability of the volume demarcations when the syringe is filled with fluid.

The disclosed device is a syringe with color volumetric measurement means on the barrel to aid in the reading of fluid volume contained in the syringe. Determining the fluid volume may be facilitated further by the addition of a colored seal member on the plunger to create greater contrast and thus increase readability and accuracy of the volume measurement.

It is accordingly the object of the present invention to provide a device, which permits individuals, even those with visual impairments, to accurately gauge the dosage level of a syringe.

It is another object of the present invention to provide an integral means that improves the readability of volume demarcations on a syringe.

It is another object of the present invention to reduce eyestrain of the operator of a syringe when determining the volume of a fluid and/or medication in a syringe.

It is another object of the present invention to reduce errors in the delivery of medication caused from syringe reading errors.

Additional objects and advantages of the present invention are apparent from the drawings and specification, which follow.

SUMMARY OF THE INVENTION

According to the present invention, the foregoing and additional objects are obtained by providing a color based high contrast volume marking system for a syringe.

A syringe having color demarcation features of the present invention includes a central body portion that is a barrel having a proximal and distal end along a central longitudinal axis that acts a reservoir for fluid inside the syringe. The side wall of the barrel is relatively transparent having volume demarcations in contrasting colors to increase the readability of the demarcations. A plunger and coupled seal member can be engaged with the proximal end of the barrel creating a liquid tight reservoir inside the syringe. The seal member can be made a contrasting color to further enhance the readability of the demarcations.

DETAILED DESCRIPTION

Figures 1, 2:
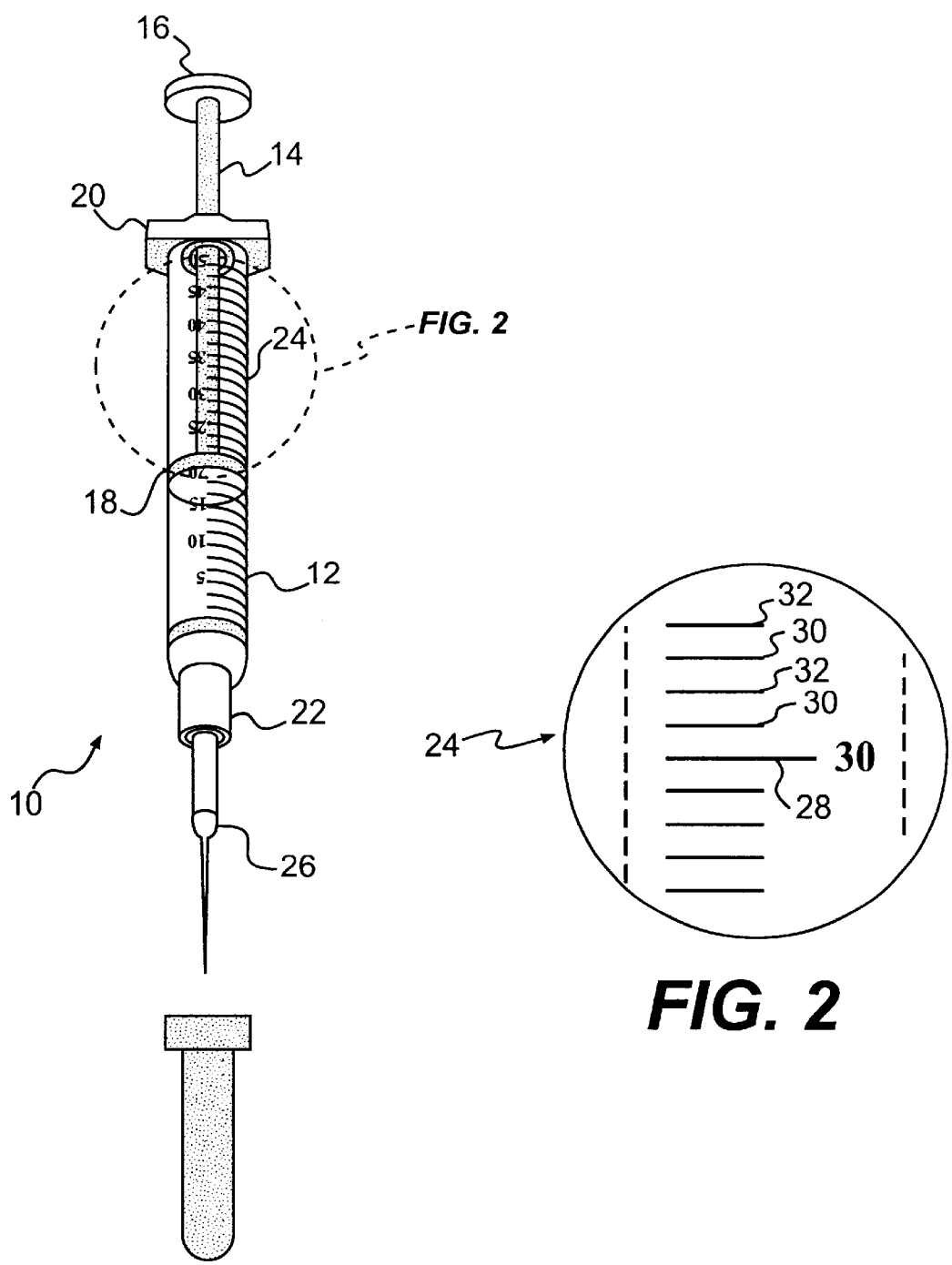
FIGS. 1 and 2 are perspective views of the preferred embodiment of the present invention.

Although, there are several embodiments that encompass the elements of the claimed invention, those shown by the drawing and written description herein represent the preferred embodiments of the present invention and are exemplary thereof and are not intended by the inventors to constitute a limitation of the same. The scope of the present invention is as stated in the attached claims and equivalents thereof.

A typical syringe used by the medical community today, is molded from thermoplastic resins. The syringe barrel is relatively transparent and usually includes volume measuring indicia embossed on the outside of the barrel in black ink. It is difficult to read the volume metric measurement of the fluid in the barrel due to the monochromatic printing of the volume demarcations and the use of a black seal on the plunger. The black plunger seal obscures the view of the black volume measuring indicia on the barrel. The present invention provides for a color based contrasting means that results in increased readability of the volume demarcations on the syringe barrel.

FIG. 1 shows a High Contrast Syringe 10 according to the present invention. The device consists of a central body portion that is a barrel 12 having a proximal and distal ends along a central longitudinal axis that acts as a reservoir for fluid inside the syringe 10. The interior side wall of the barrel 12, or fluid reservoir, is preferably circular in shape, spaced evenly from the central axis and defines an inside diameter of the reservoir for holding fluid. The proximal end of the barrel portion 12 is open to receive a plunger 14 and coupled seal member 18. The distal end has an aperture 22 for connecting a cannula or needle 26 permitting fluid exchange with the interior reservoir of the barrel 12. The plunger 14 is a separate component from the syringe barrel 12 which consists of an elongated central body portion having a longitudinal axis and two perpendicular intersecting flat members; having a proximal end member and distal end member. Said proximal end member is a disc member 16. Said distal end member is a seal member 18.

When the plunger 14 is inserted in the proximal end of the barrel 12, a flange 20 located on the perimeter of the proximal end when operated in concert with the disc member 16 on the plunger 14 assist in the engagement of the plunger 14 and movement of same inside the syringe barrel 12.

The side wall of the barrel includes demarcations 24 to measure the volume of the liquid contained within the syringe barrel 12. These demarcations 24 are used to determine the volume of the fluid inside the syringe barrel 12 as is required for delivery of the proper volume of medication or the like through the syringe 10. The demarcations 24 on the side wall of the syringe 10 in the preferred embodiment, consist of at least three contrasting colors. In this embodiment, the volume demarcations 24 extend around at least one-half of the body of the barrel 12 and are in contrasting colors.

It is the object of the contrasting demarcations 24 to provide a means for determining the volume of the fluid inside the syringe 10 in an easy and accurate manner even when the user may be somewhat visibly impaired. In this embodiment, it is preferable that the volume measuring emaciations 24 are orange 30, green 32, and blue 28 wherein every fifth unit line is blue 28 and the single individual unit lines alternate between two colors, namely orange 30 and green 32. The multi-colored demarcations 24 on the syringe 10 are easy to see and aid in the delivery of proper dosages of injected medications when used by a variety of individuals including diabetics with impaired eyesight, senior citizens and medical staff.

In the preferred embodiment volume demarcations 24 are applied to the side wall using an ink print printing process.

To one skilled in the art, it is obvious there are numerous ways to print volume demarcations 24 on the syringe barrel 12 including printing with ink, embossed, applications or molding the volume demarcations 24 in the barrel 12 which may be later printed or altered by color application to effect high contrast volume demarcations 24 on the syringe 10. It is within the scope of the present invention to include the wide variety of means for marking the volume indicia and effecting the color printing as discussed herein is merely a suggestion of the many possible ways of effecting the color gradation.

One skilled in the art would also be aware that a myriad of color combinations could be used for the present invention. Although bright contrasting colors, such as orange 30, green 32, and blue 28 are preferred for the volume demarcations 24, other colors could be used; however, the colors must be distinct enough to create the desirable effect of a contrasting palette of demarcations 24 on the syringe barrel surface 12 to aid in the reading of accurate measurements of the fluid contained therein. It should be noted that the present invention uses existing standard volume markings but improves the readability of the volume demarcations 24 by enhancing the same with the use of color.

The high color contrast means could also be employed on the seal member 18 attached to the plunger 14 when engaged with the proximal end of the barrel 12. The seal member 18 is positioned in the proximal end of the barrel 12 forming a fluid tight seal between itself 18 and the syringe barrel 12. The seal member 18 is moved along the syringe barrel 12 by applying axial force to the plunger 14 to either draw or expel fluid from the distal end. The volume of the fluid inside the barrel 12 is determined by the position of the seal member 18 in connection with the volume demarcations 24.

The syringe assembly 10 may be filled with liquid medication facilitated by the colored demarcations 24 of the present invention.

The syringe barrel 12 of the present invention may be constructed of a wide variety of rigid materials including thermoplastic materials or glass. A variety of commercially available inks may be used to create the color contrast markings on the syringe barrel 12 and color the seal member 18 on the plunger 14. Manufacturers of the syringe barrel 12 should employ only processes and products that permit the syringe 10 to be sterilized prior to use. The inks used on the present invention should also be amenable for sterilized as required for medical application. Therefore, the present invention provides a unique, useful, and reliable means for increasing the readability of the volume demarcations 24 on a syringe 10. Using color to create hyper indications of the volume demarcations 24 will aid in the accuracy of liquid medication dosage contained therein.

Many improvements, modifications, and additions will be apparent to the skilled artisan without departing from the spirit and scope of the present invention as described herein and define in the following claims.

What is claimed is:

1. A syringe barrel comprising:
   a central body portion that is a barrel having a longitudinal axis and a side wall spaced from said axis defining an inside diameter and a reservoir for retaining fluid, said barrel having an open proximal end and a distal end having a passageway therethrough in fluid communication with said reservoir;
   said side wall including a transparent portion having demarcations;
   said demarcations including color marking means of at least two different colors for improving readability of said demarcations; and said color marking means for making measurement of fluid inside said barrel.

2. The syringe barrel of claim 1 wherein said demarcations comprise volume measuring indicia.

3. The syringe barrel of claim 1 wherein said demarcations extend around at least one-half the circumference of said barrel.

4. The syringe barrel of claim 1 wherein said demarcations are at least two colors selected from the group blue, green, orange, red, yellow and black and any combinations thereof.

5. The syringe barrel of claim 1 wherein every fifth unit line of said demarcations is a high contrast color selected from the group blue, green, orange, red, yellow and black and any combinations thereof.

6. The syringe barrel of claim 1 wherein every fifth unit line of said demarcations is blue.

7. The syringe barrel of claim 1 wherein individual unit lines alternate between two colors selected from the group blue, green, orange, red, yellow and black and any combinations thereof.

8. The syringe barrel of claim 1 wherein individual unit lines alternate between two colors selected from the group orange and green.

9. The syringe barrel of claim 1 wherein every fifth unit line of said demarcations is blue; and individual emit lines alternate between two colors selected from the group orange and green.

10. The syringe barrel of claim 1 wherein said demarcations are permanently associated with the outer surface of said side wall.

11. The syringe barrel of claim 1 wherein said demarcations have a contrasting color coating means for improving readability of said demarcations on said barrel.

12. The syringe barrel of claim 1 wherein said demarcations have a contrasting color coating means for reducing eyestrain of the operator of said syringe barrel.

13. The syringe barrel of claim 1 wherein said demarcations have a contrasting color coating means for reducing inaccurate volume measurements of a fluid contained in said syringe barrel.

14. A syringe comprising:

a central body portion that is a barrel having a longitudinal axis and a side wall spaced from said axis defining an inside diameter and a reservoir for retaining fluid, said barrel having an open proximal end and a distal end having a passageway therethrough in fluid communication with said reservoir;

said side wall including a transparent portion having demarcations; said demarcations including color marking means of at least two different colors for improving readability of said demarcations;

said color marking means for making measurement of fluid inside said barrel; a plunger;

said plunger slidably positionable in fluid-tight engagement inside said barrel;

said plunger having an elongated central body portion having a longitudinal axis;

said plunger having a proximal end connected to a disc member; and said plunger having a distal end connected to a seal member.

15. The plunger of claim 14 wherein said body portion has two perpendicular intersecting flat members.

16. The plunger of claim 14 wherein said seal member is a high contrast color selected from the group blue, green, orange, red, yellow and black and any combinations thereof.

17. The plunger of claim 14 wherein said seal member has a contrasting color coating means for improving readability of said demarcations on said barrel.

18. The plunger of claim 14 wherein said seal member has a contrasting color coating means for reducing eyestrain of the operator of said syringe barrel.

19. The plunger of claim 14 wherein said seal member has a contrasting color coating means for reducing inaccurate volume measurements of a fluid contained in said syringe barrel.

* * * * *